(12) United States Patent
Curran et al.

(10) Patent No.: US 6,727,390 B2
(45) Date of Patent: Apr. 27, 2004

(54) FLUOROUS PHOSPHINES AND PHOSPHINE OXIDES

(75) Inventors: Dennis P. Curran, Pittsburgh, PA (US); Qisheng Zhang, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/952,188

(22) Filed: Sep. 14, 2001

(65) Prior Publication Data

US 2002/0183521 A1 Dec. 5, 2002

Related U.S. Application Data

(60) Provisional application No. 60/281,646, filed on Apr. 5, 2001.

(51) Int. Cl.$^7$ .................................................. C07F 9/02

(52) U.S. Cl. .............................. 568/14; 568/16; 556/21

(58) Field of Search ............................. 568/8, 14, 16, 568/17; 556/13, 21, 136, 138

(56) References Cited

U.S. PATENT DOCUMENTS

| | | | | |
|---|---|---|---|---|
| 3,975,447 A | * | 8/1976 | Knoth et al. ................... | 568/14 |
| 4,124,456 A | * | 11/1978 | Yagupolsky et al. ......... | 205/420 |
| 4,454,233 A | | 6/1984 | Wang | |
| 4,454,349 A | * | 6/1984 | Tamborski et al. ............ | 568/13 |
| 5,401,847 A | | 3/1995 | Glazer | |
| 5,442,084 A | * | 8/1995 | Lal ............................. | 558/141 |
| 5,463,082 A | | 10/1995 | Horvath | |
| 5,527,960 A | * | 6/1996 | Aoyama ...................... | 564/12 |
| 5,777,121 A | | 7/1998 | Curran | |
| 5,798,032 A | | 8/1998 | Khan | |
| 5,859,247 A | | 1/1999 | Curran | |
| 6,156,896 A | | 12/2000 | Curran | |

OTHER PUBLICATIONS

CA:127:155791 abs of Chem Communications by Fawcett (12) pp. 1127–1128 1997.*
Journal of Organic Chemistry by Zhang et al 65 pp. 8866–8873 2000.*
Bhattacharyya, P.; Gudmunsen, D., et.al. Phosphorus (III) Ligands with Fluorous Ponytails. J. Chem. Soc., Perkin Trans. 1 1997, 3609–3612.
Curran, D.P. Strategy–Level Separations in Organic Synthesis: From Planning to Practice. Angew. Chem., Int. Ed. Eng. 1998, 37, 1175–1196.
Curran, D. P. Fluorous Synthesis: An Alternative to Organic Synthesis and Solid Phase Synthesis for the Preparation of Small Organic Molecules. The Cancer Journal 1998, 4 Supp. 1, S73–76.
Curran, D. P. Parallel Synthesis with Fluorous Reagents and Reactants. Med. Res. Rev. 1999, 19, 432–438.

Fawcett, J.; Hope, E. G. et al. Platinum Group Metal Complexes of Arylphosphine Ligands Containing perfluoroalkyl Ponytails; Crystal Structures of [RhCl2(eta(5)–C5Me5) {P(C6H4C6F13–4)3}] and Cis and Trans—[PtC12 {P(C6H4C6F13–4)3}2]. j. cHEm.sOC., Dalton Trans. 1998, 3751–3763.

Francio, G.; Leitner, W. Highly Regio–and Enantio–Selective Rhodium–Catalysed Asymmetric hydroformylation without organic Solvents. Chem. Commun. 1999, 1663–1664.

Horvath, I.T. Fluorous Biphase Chemistry. Acc. Chem. res. 1998, 31, 641–650.

Hope, E. G., Kemmitt, R. D. W. et. al. Synthesis and Coordination Chemistry of meta—Perfluoroalkyl—Derivatised Triarylphosphines. Polyhedron 1999, 18, 2913–2917.

Hope, E. G. K. et. al. The Rhodium Catalysed Hydrogenation of Styrene in the Fluorous Biphase. J. Fluorine Chem. 1999, 99, 197–200.

(List continued on next page.)

Primary Examiner—Jean F. Vollano
(74) Attorney, Agent, or Firm—Bartony & Hare, LLP

(57) ABSTRACT

A method of increasing the fluorous nature of a compound includes the step of reacting the compound with or tagging the compound with at least one of a second compound having the formula:

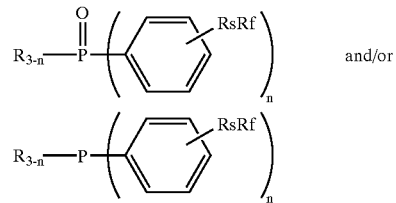

and/or wherein R is an alkyl group or an aryl group, n is 1, 2 or 3 and Rs is a spacer group and Rf is a branched fluorous group. A chemical compound having the general formula:

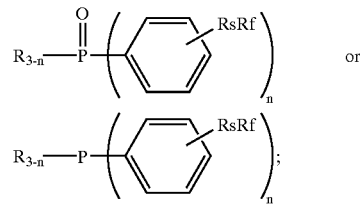

or wherein n, Rs and Rf are defined above.

29 Claims, 5 Drawing Sheets

OTHER PUBLICATIONS

Horvath, I. T.; Kiss, G. et al. Molecular Engineering in Homogeneous Catalysis: One—Phase Catalysis coupled with Biphase Catalyst Separation. The Fluorous—Soluble HRh(CO) {P[CH2CH2(CF2)5CF3]3}3 Hydroformylation System. J. Am. Chem. Soc. 1998, 120, 3133–3143.

Kainz, S.; Brinkmann, A. et. al. Iridium—Catalyzed Enantioselective Hydrogenation of Imines in Supercritical Carbon Dioxide. J. Am. Chem. Soc. 1999, 121, 6421–6429.

Richter, B.; Deelman, B. J.; Van Koten, G. Fluorous Biphasic Hydrogenation of 1–Alkenes Using Novel Fluorous Derivatives of Wilkinson's Catalyst. J. Mol. Catal. A Chem. 1999, 145, 317–321.

Sinou, D.; Pozzi, G.; Hope, E. G.; Stuart, A. M. A Convenient Access to Triarylphosphines with Fluorous Phase Affinity. Tetrahedron Lett. 1999, 40, 849–852.

* cited by examiner

1a

| | n |
|---|---|
| 2a | 3 |
| 2b | 2 |
| 2c | 1 |

| | n |
|---|---|
| 3a | 3 |
| 3b | 2 |
| 3c | 1 |

| | n |
|---|---|
| 4a | 3 |
| 4b | 2 |
| 4c | 1 |

| | n |
|---|---|
| 1a | 3 |
| 1b | 2 |
| 1c | 1 |

| | n |
|---|---|
| 5a | 3 |
| 5b | 2 |
| 5c | 1 |

| | n | yield |
|---|---|---|
| 5a | 3 | 49% |
| 5b | 2 | 68% |
| 5c | 1 | 51% | linear (from oxidation)

| | n | yield |
|---|---|---|
| 11a | 3 | 86% |
| 11b | 2 | 90% |
| 11c | 1 | 100% | branched (from Figure 5)

$$(Ph)_{3-n}-\overset{O}{\underset{\|}{P}}\left(\underset{}{\bigcirc}-CH_2C(CF_3)_2C_3F_7\right)_n$$

| | n |
|---|---|
| 12a | 3 |
| 12b | 2 |
| 12c | 1 |

13a-c linear
14a-b branched

| Entry | Phosphine | Product | Rfh | n | Yield (%) |
|---|---|---|---|---|---|
| 1 | 1a | 13a | $(CH_2)_2C_6F_{13}$ | 3 | 85 |
| 2 | 1b | 13b | $(CH_2)_2C_6F_{13}$ | 2 | 83 |
| 3 | 1c | 13c | $(CH_2)_2C_6F_{13}$ | 1 | 85 |
| 4 | 5a | 14a | $CH_2C(CF_3)_2C_3F_7$ | 3 | 82 |
| 5 | 5b | 14b | $CH_2C(CF_3)_2C_3F_7$ | 2 | 86 |

US 6,727,390 B2

FLUOROUS PHOSPHINES AND PHOSPHINE OXIDES

RELATED REFERENCES

The present patent application claims priority of U.S. Provisional Patent Application Serial No. 60/281,646 entitled FLUOROUS PHOSPHINES AND PHOSPHINE OXIDES and filed Apr. 5, 2001, the disclosure of which is incorporated herein by reference.

GOVERNMENT INTEREST

This invention was made with government support under grant R01 GM33372 awarded by the National Institutes of Health. The government has certain rights in this invention.

BACKGROUND OF THE INVENTION

The present invention relates to fluorous phosphine compounds and to methods of increasing the fluorous nature of chemical entities using such fluorous phosphine compounds, and, particularly, to branched fluorous phosphine compounds and to methods of increasing the fluorous nature of chemical entities using such branched fluorous phosphine compounds.

References set forth herein may facilitate understanding of the present invention or the background of the present invention. Inclusion of a reference herein, however, is not intended to and does not constitute an admission that the reference is available as prior art with respect to the present invention.

Fluorous techniques for the synthesis of small organic molecules are becoming increasingly useful as more and more fluorous compounds are synthesized and studied. These techniques are attractive for strategic separation of reaction mixtures since fluorous-tagged compounds can be quickly separated from non-tagged compounds in, for example, binary liquid-liquid and solid-liquid extractions. Fluorous tagging is discussed, for example, in U.S. Pat. Nos. 5,859,247, 5,777,121, and 6,156,896, and U.S. patent application Ser. No. 09/506,7796, all assigned to the assignee of the present invention, the disclosures of which are incorporated herein by reference. The fluorine content of a fluorous molecule is an important aspect to be balanced to obtain suitable performance during both the reaction and the separation. Opposing needs during reaction and separation can be thought of as dividing the fluorous field into two branches or techniques, which have recently been termed "heavy fluorous" and "light fluorous". Those two techniques are actually ends of a continuum with a considerable gray area in between.

On the heavy fluorous end, fluorous techniques strive for very high partition coefficients in liquid-liquid separation, requiring fluorous reagents and catalysts with large numbers of fluorine atoms. Heavy fluorous techniques afford easy separation, but the large numbers of fluorines tend to render the fluorous compounds insoluble in typical organic reaction solvents. Fluorous cosolvents are thus used which have poor dissolving power for organic compounds, so the modification and optimization of reaction conditions is often required. However, once suitable conditions are found, the resulting heavy fluorous techniques are very powerful, especially when applied to catalytic reactions.

On the light fluorous end, the number of fluorine atoms are reduced to provide fluorous compounds that have properties more similar to their organic parents. While reduction of the fluorine content can allow the use of standard literature reaction conditions with little or no modification, the reduced fluorine content compromises the separation of fluorous from non-fluorous components by liquid-liquid extraction. However, the recently introduced technique of fluorous solid phase extraction is proving far superior to liquid-liquid extractions for separation of compounds with fewer fluorines. See, for example, a) Curran, D. P.; Hadida, S.; He, M. *J. Org. Chem.* 1997, 62, 6714. b) Curran, D. P.; Luo, Z. Y. *J. Am. Chem. Soc.* 1999, 121, 9069. c) Curran, D. P.; Hadida, S.; Kim, S. Y.; Luo, Z. Y. *J. Am. Chem. Soc.* 1999, 121, 6607. d) Curran, D. P.; Hadida, S.; Studer, A.; He, M.; Kim, S. -Y.; Luo, Z.; Larhed, M.; Hallberg, M.; Linclau, B. In *Combinatorial Chemistry: A Practical Approach*; H. Fenniri, Ed.; Oxford Univ Press: Oxford, in press; Vol. 2. Light fluorous techniques are especially useful for small scale and discovery oriented research, including parallel synthesis applications and so-called techniques of fluorous synthesis. See, for example, a) Curran, D. P. *Med. Res. Rev.* 1999, 19, 432; b) Studer, A.; Hadida, S.; Ferritto, R.; Kim, S. Y.; Jeger, P.; Wipf, P.; Curran, D. P. *Science* 1997, 275, 823. c) Curran, D. P. *The Cancer Journal* 1998, 4 Supp. 1, S73.

Fluorous biphasic catalysis (FBC) was the original fluorous technique introduced in 1994 by Horváth and Rábai, and that technique is finding increasing utility in the catalysis community. Horváth, I. T.; Rábai, J. *Science* 1994, 266, 72. Most of the work in the area of fluorous biphasic catalysis involves the use of fluorous phosphines and phosphites. Mathivet, T.; Monflier, E.; Castanet, Y.; Mortreux, A.; Couturier, J. L. *Tetrahedron Lett.* 1999, 40, 3885. The original trialkylphosphine ligand [$P(CH_2CH_2C_6F_{13})_3$] introduced by Horváth and Rábai has proved useful in a number of reactions catalyzed by rhodium and iridium. See, for example, a) Guillevic, M. A.; Rocaboy, C.; Arif, A. M.; Horváth, I. T.; Gladysz, J. A. *Organometallics* 1998, 17, 707. b) Horváth, I. T.; Kiss, G.; Cook, R. A.; Bond, J. E.; Stevens, P. A.; Rabai, J.; Mozeleski, E. J. *J. Am. Chem. Soc.* 1998, 120, 3133. c) Juliette, J. J. J.; Rutherford, D.; Horváth, I. T.; Gladysz, J. A. *J. Am. Chem. Soc.* 1999, 121, 2696. d) Li, C. B.; Nolan, S. P.; Horváth, I. T. *Organometallics* 1998, 17, 452. e) Smith, D. C.; Stevens, E. D.; Nolan, S. P. *Inorg. Chem.* 1999, 38, 5277.

More recently, a number of fluorous analogs of triphenylphosphine have appeared, and several of these are shown in FIG. 1. Phosphine 1a was introduced by Leitner for reactions in supercritical carbon dioxide and has also found use in an FBC variant of the popular palladium catalyzed allylic substitution (Tsuji/Trost) reaction. Kainz, S.; Koch, D.; Baumann, W.; Leitner, W. *Angew. Chem., Int. Ed. Engl.* 1997, 36, 1628; Kling, R.; Sinou, D.; Pozzi, G.; Choplin, A.; Quignard, F.; Busch, S.; Kainz, S.; Koch, D.; Leitner, W. *Tetrahedron Lett.* 1998, 39, 9439. Related phosphine 2a, lacking the ethylene spacer, has been used by Knochel as a ligand for palladium catalyzed Negishi couplings and Heck reactions. Betzemeier, B.; Knochel, P. *Angew. Chem., Int. Ed. Engl.* 1997, 36, 2623. Hope and coworkers have prepared families of phosphines bearing one, two, and three fluorous chains in both the para (2a–c) and meta (3a–c) series and studied the properties of several organometallic complexes of these ligands. See, a) Fawcett, J.; Hope, E. G.; Kemmitt, R. D. W.; Paige, D. R.; Russell, D. R.; Stuart, A. M.; ColeHamilton, D. J.; Payne, M. J. *Chem. Commun.* 1997, 1127. b) Bhattacharyya, P.; Gudmunsen, D.; Hope, E. G.; Kemmitt, R. D. W.; Paige, D. R.; Stuart, A. M. *J. Chem. Soc., Perkin Trans.* 1 1997, 3609. c) Fawcett, J.; Hope, E. G.; Kemmitt, R. D. W.; Paige, D. R.; Russell, D. R.; Stuart, A. M. *J. Chem. Soc. Dalton Trans.* 1998, 3751. d)

Hope, E. G.; Kemmitt, R. D. W.; Stuart, A. M. *J. Chem. Soc. Dalton Trans*. 1998, 3765. e) Sinou, D.; Pozzi, G.; Hope, E. G.; Stuart, A. M. *Tetrahedron Lett*. 1999, 40, 849. f) Hope, E. G.; Kemmitt, R. D. W.; Paige, D. R.; Stuart, A. M.; Wood, D. R. W. *Polyhedron* 1999,18, 2913. g) Hope, E. G.; Kemmitt, R. D. W.; Paige, D. R.; Stuart, A. M. *J. Fluorine Chem*. 1999, 99, 197. Ligands with a silyl spacer (see 4a) have been synthesized and studied by van Koten and coworkers. See, for example, a) Richter, B.; Deelman, B. J.; van Koten, G. *J. Mol. Catal. A Chem*. 1999, 145, 317. b) Richter, B.; Spek, A. L.; vanKoten, G.; Deelman, B. J. *J. Am. Chem. Soc*. 2000, 122, 3945. c) Richter, B.; deWolf, E.; vanKoten, G.; Deelman, B. J. *J. Org. Chem*. 2000, 65, 3885. d) deWolf, E.; Richter, B.; vanKoten, G.; Deelman, B. J. *J. Org. Chem*. 2000, 65, 5424.

Given the utility of recently developed fluorous techniques, it is highly desirable to develop additional fluorous compounds that can be used in such techniques.

SUMMARY OF THE INVENTION

In one aspect, the present invention provides a method of increasing the fluorous nature of a compound. The method includes the step of reacting the compound with or tagging the compound with at least one of a second compound having the formula:

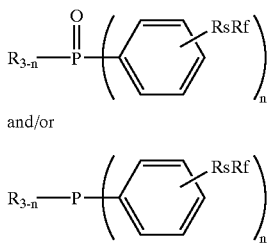

and/or wherein R is an alkyl group or an aryl group, n is 1, 2 or 3 and Rs is a spacer group and Rf is a branched fluorous group.

In another aspect, the present invention provides a chemical compound having the general formula:

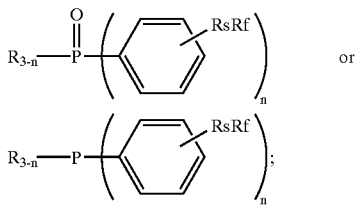

wherein n, Rs and Rf are defined above.

Spacer groups suitable for use in the present invention preferably act to neutralize, reduce or compensate for the electron withdrawing effect of the fluorous group Rf. Rs can, for example, be an $C_1$–$C_{12}$ alkylene group or (—$CH_2$—)$_x$ wherein x is 1–12. More preferably, Rs is a $C_1$–$C_6$ alkylene group.

The terms "alkyl", "aryl" and other groups as used herein refer generally to both unsubstituted and substituted groups unless specified to the contrary. Unless otherwise specified, alkyl groups are hydrocarbon groups and are preferably $C_1$–$C_{15}$ (that is, having 1 to 15 carbon atoms) alkyl groups, and more preferably $C_1$–$C_{10}$ alkyl groups, and most preferably $C_1$–$C_6$, and can be branched or unbranched, acyclic or cyclic. The above definition of an alkyl group and other definitions apply also when the group is a substituent on another group. The term "aryl" refers generally to phenyl (Ph) or napthyl, substituted or unsubstituted. Alkyl groups can, for example, be substituted with one or more groups including, but not limited to, a halogen, an alkoxy group and/or, an aryl group. Aryl groups can, for example, be substituted with one or more groups including, but not limited to, a halogen, an alkoxy group and/or an alkyl group. The term "alkoxy group" as used herein refers generally to —OR, wherein R is an alkyl group.

As used herein, the term "fluorous", when used in connection with an organic (carbon-containing) molecule, moiety or group, refers generally to an organic molecule, moiety or group having a domain or a portion thereof rich in carbon-fluorine bonds (for example, hydrofluoroalkyl groups and perfluoroalkyl groups). As used herein, the term "perfluoroalkyl groups" refers generally to alkyl groups in which all hydrogen atoms bonded to carbon atoms have been replaced by fluorine atoms. The terms "fluorohydroalkyl groups" and "hydrofluoroalkyl groups" include organic compounds in which at least one hydrogen atom bonded to a carbon atom has been replaced by a fluorine atom. Flourous group Rf preferably has a molecular weight in the range of approximately 200 to approximately 1000. More preferably, Rf has a molecular weight in the range of approximately 200 to approximately 550.

The term "branched" as use herein in connection with hydrofluoroalkyl groups and perfluoroalkyl groups refers generally to a group that has at least one carbon atom attached to at least three other carbon atoms. The branched hydrofluoroalkyl groups and perfluoroalkyl groups of the present invention can be cyclic or acyclic. The branched fluorous groups of the present invention preferably have no C—H bonds β to a carbon-fluorine (C—F) bond to eliminate the possibility of HF elimination reaction of the tag under strongly basic conditions. An example of a C—H bond β to a C—F bond is provided below.

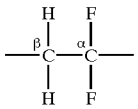

In several embodiments in which Rs is an alkylene group, Rf is branched at the carbon atom adjacent Rs such that there is no C—H bond in Rs that is β to a C—F bond. Such branched fluorous groups for use in the present invention include, but are not limited to, —$C(CF_3)_2C_3F_7$ and —$C(CF_3)_2C_4F_9$ or generally, —$CRf^1Rf^2(CF_2Rf^3)$ wherein $Rf^1$, $Rf^2$ and $Rf^3$ are independently (the same or different) a fluorous group (preferably, a hydrofluoroalkyl group or a perfluoroalkyl group). $Rf^1$ and $Rf^2$ can also form a hydrofluoroalkyl ring or a perfluoroalkyl ring of 3 to 12 members (preferably, 5 to 6 members). Alternatively, $Rf^1$ and $Rf^3$ can form a hydrofluoroalkyl ring or a perfluoroalkyl ring of 3 to 12 members (preferably, 5 to 6 members). Likewise, $Rf^2$ and $Rf^3$ can form a hydrofluoroalkyl ring or a perfluoroalkyl ring of 3 to 12 members (preferably, 5 to 6 members). In the case of —$C(CF_3)_2C_3F_7$, $Rf^1$ is —$CF_3$, $Rf^2$ is —$CF_3$ and $Rf^3$ is —$C_2F_5$.

As used herein, the term "tagging" refers generally to attaching a fluorous moiety or group (referred to as a "fluorous tagging moiety" or "tagging group") to a compound to create a "fluorous tagged compound". Separation of the tagged compounds of the present invention can be achieved by using fluorous separation techniques that are based upon differences between/among the fluorous nature of a mixture of compounds. As used herein, the term "fluorous separation technique" refers generally to a method that is used to separate mixtures containing fluorous molecules or organic molecules bearing fluorous domains or tags from each other and/or from non-fluorous compounds based predominantly on differences in the fluorous nature of molecules (for example, size and/or structure of a fluorous molecule or domain or the absence thereof). Fluorous separation techniques include but are not limited chromatography over solid fluorous phases such as fluorocarbon bonded phases or fluorinated polymers. See, for example, Danielson, N. D. et al., "Fluoropolymers and Fluorocarbon Bonded Phases as Column Packings for Liquid Chromatography," *J. Chromat.*, 544, 187–199 (1991). Examples of suitable fluorocarbon bonded phases include commercial Fluofix® and Fluophase™ columns available from Keystone Scientific, Inc. (Bellefonte, Pa.), and FluoroSep™-RP-Octyl from ES Industries (Berlin, N.J.). Other fluorous separation techniques include solid-liquid (or solid phase) extraction and liquid-liquid based separation methods such as liquid-liquid extraction or countercurrent distribution with a fluorous solvent and an organic solvent.

The compounds of the present invention are particularly suitable for creating fluorous metal ligands. In that regard, the present invention also provides metal complexes of a metal and at least one phosphine and/or phosphine oxide as described above. The metal is preferably rhodium, platinum, palladium, nickel, iron, ruthenium, osmium, cobalt or iridium.

In still a further aspect, the present invention provides a method of synthesizing a branched fluorous phosphine comprising the steps of: reacting a fluoroalkene with a metal fluoride; adding an alkylating agent to produce a fluorous halo arene; converting the fluorous halo arene to an organometallic derivative thereof; and reacting the organometallic derivative with $R_{3-n}P(Z^3)_n$ wherein $Z^3$ is a leaving group and wherein R is an alkyl group or an aryl group.

DETAILED DESCRIPTION OF THE INVENTION

Figure 2:
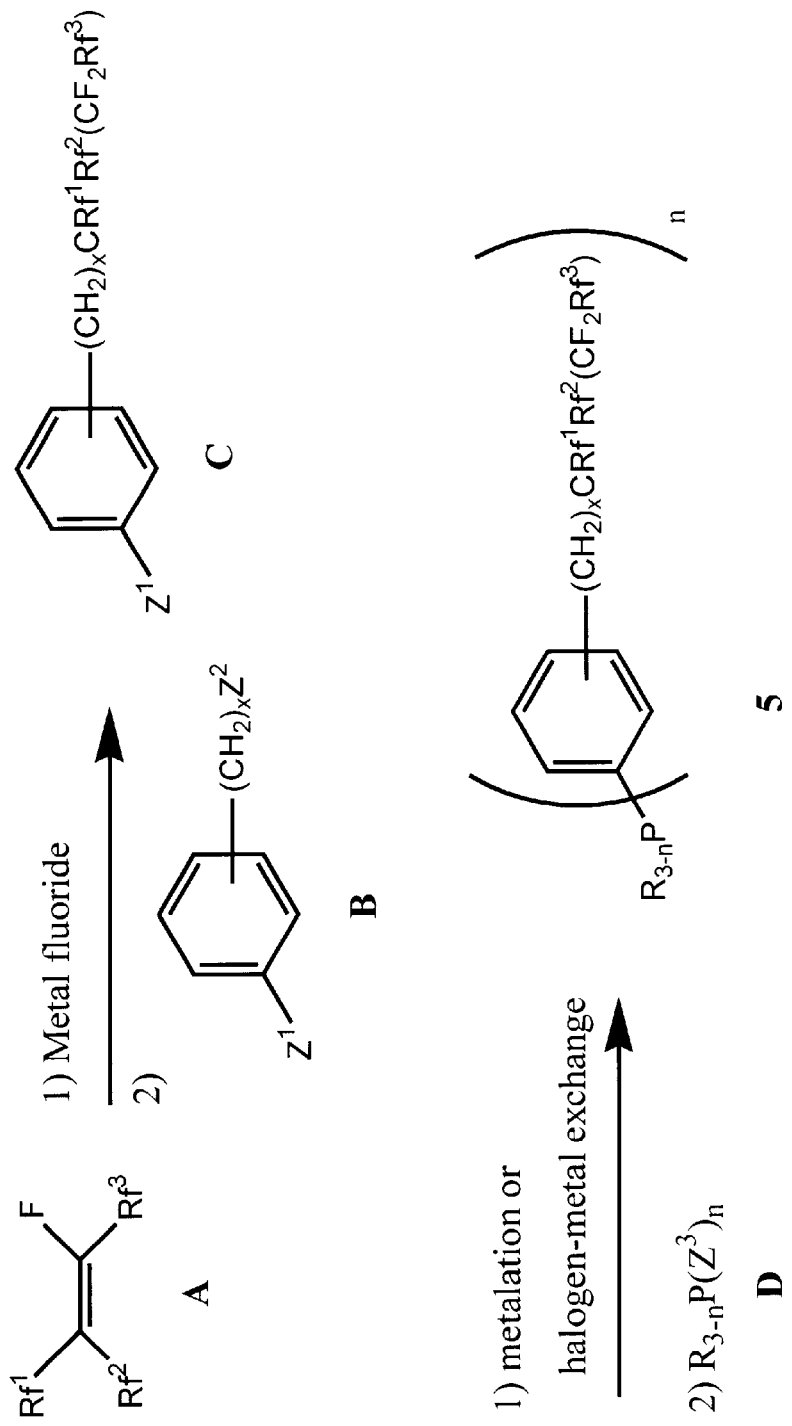
FIG. 2 illustrates an embodiment of a synthetic route to the branched fluorous phosphines of the present invention.

The phosphines and phosphine oxides of this invention can be synthesized by the general route shown in FIG. 2 (showing the case in which Rf is —$CRf^1Rf^2(CF_2Rf^3)$). Addition of a metal fluoride to a perfluoroalkene A generates a reactive intermediate in situ which is then used to react with an alkylating agent B to produce arene C. In this reaction, preferred metals are alkali metals, especially sodium, potassium, and most preferably, cesium. $Z^1$ is bromine or iodine, and $Z^2$ is a leaving group suitable for displacement at a saturated carbon atom as known in the art, such as chloride, bromide, iodide, mesylate, tosylate, etc. Preffered solvents are polar solvents such as sulfolane, or more preferably, DMF. Fluorous arene C is then converted to an organometallic derivative either by metallation (for example, with lithium metal or magnesium metal) or halogen-metal exchange (for example, with n-butyllithium, sec-butyllithium, or tert-butyllithium). Reaction of the so-formed intermediate with $R_{3-n}P(Z^3)_n$ D in the appropriate stoichiometry generates the fluorous phosphine 5. In this reaction, $Z^3$ is a leaving group as known in the art that is suitable for displacement at a saturated phosphorous atom, such as halogen, chalcogen, alkoxy, aryloxy, or amido. Preferred leaving groups include Cl, OMe, OEt, $NMe_2$, and $NEt_2$. R is an alkyl group or an aryl group as described above.

In general, the fluorous phosphine and phosphine oxide can be interconverted by using standard reaction conditions that are used for the non-fluorous analogs. For example, the fluorous phosphine oxides can readily be prepared by oxidation of the corresponding phosphines with air, hydrogen peroxide or many other oxidants under standard procedures. For some uses, such as the Wittig reaction and related reactions, the fluorous phosphine precursor is converted during the course of the reaction to the corresponding fluorous phosphine oxide. In such cases, the fluorous phosphine can be regenerated by reduction of the phosphine oxide with lithium aluminum hydride or other standard reagents. Metal complexes of the fluorous phosphines with metals can also be prepared by using the standard reaction conditions that are used for non-fluorous phosphines as known in the art. However, in cases where the fluorous phosphine contains a large number of fluorines (typically 27 or more), it may sometimes be beneficial to add a fluorinated solvent or cosolvent (for example, benzotrifluoride) to increase the solubility of the fluorous component in the reaction medium.

The synthesis and study of two related families of linear 1*a–c* and branched 5*a–c* fluorous phosphines shown was undertaken in the present studies. The fluorous-tagged phosphines were then used to produce fluorous catalysts (that is, metal complexes of the flourous-tagged phosphines) for studies of allylations with fluorous allylstannane.

Figure 3:
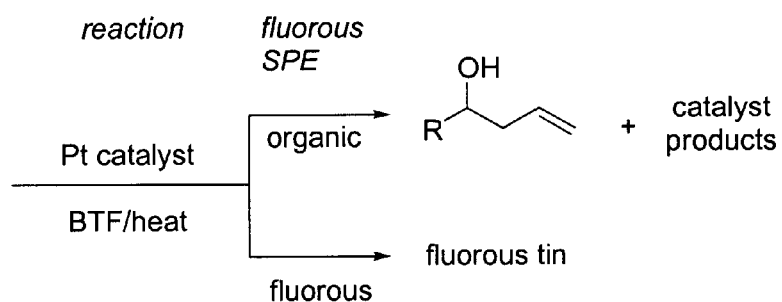
FIG. 3 illustrates platinum catalyzed allylations with a fluorous allylstannane.

In that regard, reagents 6*a,b* bearing a propylene spacer were prepared and used in the platinum catalyzed allylation shown in FIG. 3. Small libraries of alcohols were conveniently prepared by parallel synthesis with separation of the fluorous tin residues by solid phase extraction over fluorous reverse phase silica gel. A non-fluorous platinum catalyzed procedure (using $Cl_2Pt(PPh_3)_2$) was not very practical for parallel synthesis as fluorous solid phase extraction did not separate any remnant of the catalyst from the desired organic products in FIG. 3. Fluorous platinum catalysts derived from the fluorous phophine ligands of the present invention exhibited good organic solubility and promoted allylations of aldehydes with a fluorous allylstannane. Moreover, all the fluorous components of the reaction mixtures (including the catalyst remnants) can be removed by solid phase extraction.

Figure 4:
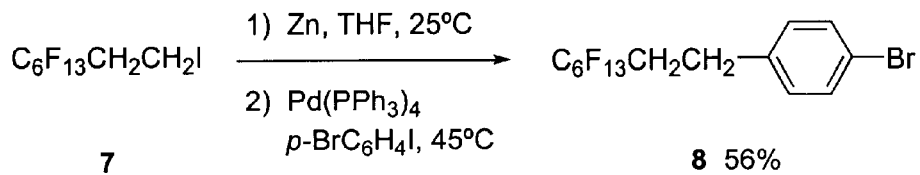
FIG. 4 illustrates an embodiment of a synthetic route to linear fluorous phoshpines.
Figure 4:
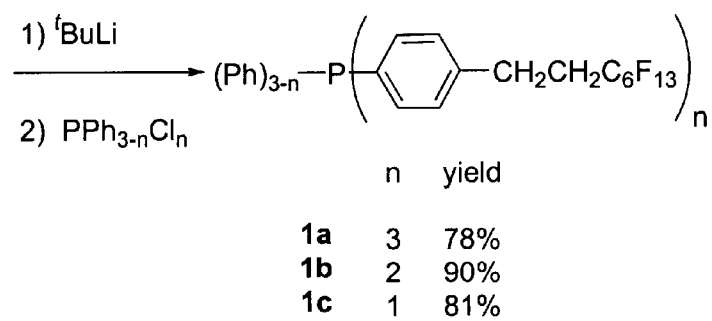
Figure 5:
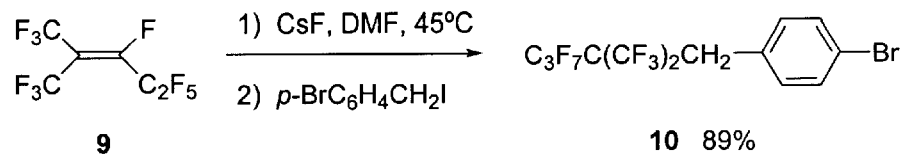
FIG. 5 illustrates a representative example of synthesis of branched fluorous phosphines.
Figure 5:
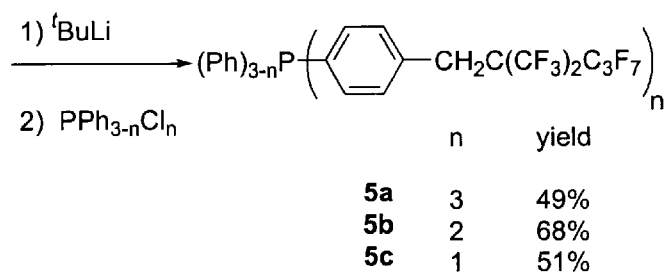

The syntheses of two related series of phosphines are shown in FIGS. 4 and 5. Phosphine 1*a* was already known from the work of Leitner. During the course of the studies of the present invention, several modifications were made to synthesis of Leitner in producing phosphines 1*a–c* (FIG. 4). The Leitner protocol (not shown) for synthesis of aryl bromide 8 calls for coupling of perfluorohexylethyl iodide 7 with the Grignard reagent derived from 1,4- dibromobenzene. This provides the aryl bromide 8 along with substantial amount of Wurtz coupled product ($C_6F_{13}CH_2CH_2CH_2CH_2C_6F_{13}$). A convenient procedure was developed to separate these on small scale by using fluorous silica, but large scale separation is difficult because the two compounds have similar polarities and boiling points. It was found that palladium catalyzed coupling of an organozinc reagent derived from 7 with 1-iodo-4-bromobenzene gave a much cleaner product 8. Little or no Wurtz coupled product was obtained provided that the temperature was not allowed to rise above 25° C. during formation of the zinc reagent. The coupling process was accomplished at 45° C.; again, higher temperatures gave lower yields. Bromide 8 can be reliably synthesized by this procedure in about 56% yield (after distillation) on scales up to at least 30 g. The lower homolog bearing $C_4F_9$ group and the meta-isomer were synthesized in comparable yields by the same procedure (not shown).

Leitner prescribes the use of n-BuLi for the generation and reaction of the lithium reagent derived from 8, but improved results were achieved with t-BuLi. Halogen/lithium exchange followed by quenching with $PCl_3$ provided Leitner's phosphine 1a in 78% isolated yield. Likewise, quenching with $PhPCl_2$ and $Ph_2PCl$ provided the new phosphines 1b and 1c in even higher yields.

Fluorous tags including branched fluorocarbons are of interest because branched tags can confer improved solubility. In addition, the branched tags prepared in the present studies have no C—H bonds β to fluorine. This design feature eliminates any possible HF elimination reactions of the tag under strongly basic conditions.

To prepare the requisite aryl bromides with branched tags, a procedure recently reported by Chambers and coworkers was modified as illustrated in FIG. 5. Chambers, R. D.; Magron, C.; Sandford, G. *J. Chem. Soc., Perkin Trans. 1* 1999, 283. Chambers et al. reported that reaction of p-bromobenzyl bromide and perfluoroalkene 9 with cesium fluoride in sulfolane provided the fluoroalkylated product 10 in 62% yield, contaminated with substantial amounts of p-bromobenzyl fluoride. The present inventors have discovered that this direct fluoride substitution product can be suppressed by using p-bromobenzyl iodide and by changing the solvent to DMF. This procedure reduced the reaction time from 8 days to less than 4 days, and improved the yield of 10 to 89%.

Figure 6:
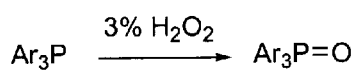
FIG. 6 illustrates oxidation of fluorous phosphines to synthesize fluorous phosphine oxides.
Figure 6:
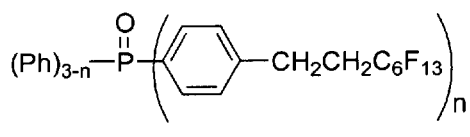

Metallation of 10 and reaction with $PCl_3$, $PhPCl_2$, and $Ph_2PCl$ then provided the phosphines 5a–c with branched tags in acceptable yields (49–68%). In these experiments, significant amounts of the phosphine oxides 12a–c were also obtained (12–20%, see Eq 4), and these could be reduced to provide additional phosphine (see below). The branched phosphines 5a–c are not isomers of the linear phosphines 1a–c; they have one fewer $CH_2$ group. However, both series have the same number of "spacer" carbons (2) between the aryl ring and the fluoroalkyl group(s). Authentic samples of the phosphine oxides 11a–c derived from 1a–c were prepared in high yields by standard oxidation with hydrogen peroxide, as shown in FIG. 6.

Figure 1:
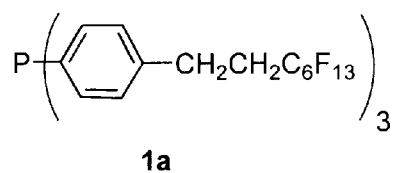
FIG. 1 illustrates several currently available fluorous phosphines and some new phosphines of the present invention.
Figure 1:
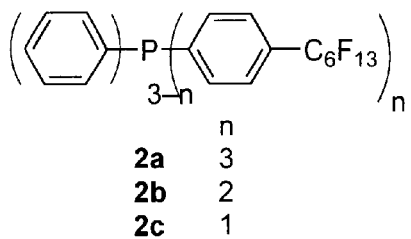
Figure 1:
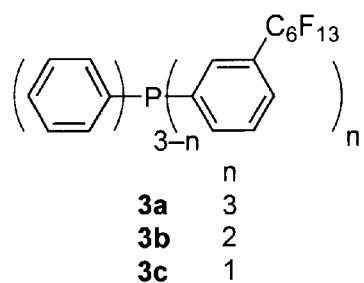
Figure 1:
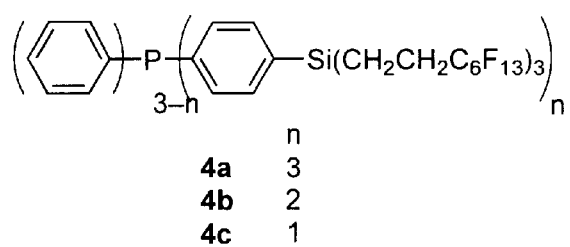
Figure 1:
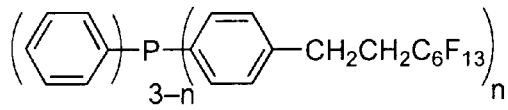
Figure 1:
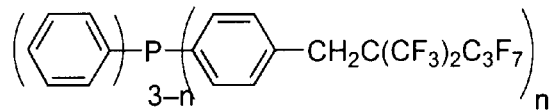

$^{31}P$ NMR experiments showed that the chemical shifts of the new phosphines were all in a narrow range between triphenylphosphine (δ=−5.0) and tri(p-tolyl)phosphine (δ=−7.26). Indeed, the range of $^{31}P$ chemical shifts of the phosphines of the present invention and all those in FIG. 1 is very small (<3 ppm).

The phosphines and phosphine oxides were evaluated by analytical HPLC to assess their potential for removal by solid phase extraction. Pure samples were injected on a commercial Fluofixm™ column (bonded phase:—$Si(Me)_2 CH_2CH_2CH_2C(CF_3)_2C_3F_7$). Under isocratic conditions, the compounds with differing numbers of fluorous tags were so widely separated as to make collective analysis impossible. Therefore a gradient starting with 80% MeOH/$H_2O$ increasing to 100% MeOH over 30 min (flow rate, 1.5 ml/min) was used. THF was then introduced in a second gradient to reach a final solvent composition of 90% MeOH/10% THF after an additional 30 min.

The retention times of the tagged phosphines and phosphine oxides are shown in Table 1. Triphenylphosphine and triphenylphosphine oxide come off with the solvent front under these conditions (retention time=1.6 min), and experience suggests that most other organic compounds would do likewise. The tagged phosphines and phosphine oxides then emerge in groups based on the number of tags. This was expected since fluorous silica separates molecules primarily by fluorine content. Molecules with a single chain ("c" series) emerge at 9–14 min, those with two chains ("b" series) emerge at 28–30 min, and those with three chains ("a" series) emerge at 38–42 min. Since the solvent changes at 30 min (THF is introduced), the absolute spacing between the groups is not directly comparable. Indeed, THF is a relatively powerful eluting solvent for fluorous molecules, and we suspect that on any absolute scale the gap between triply (a) and doubly (b) tagged molecules would be larger than the gap between doubly (b) and singly (c) tag molecules. However, these gaps are so large as to make them difficult to measure. These retention times show that fluorous phosphines and phosphine oxides can be readily separated from organic compounds by fluorous solid phase extraction.

TABLE 1

Retention Times (min) of Phosphines and Phosphine oxides on a Fluofix Column[a]

| Phosphine or Phosphine Oxide | a | b | c |
| --- | --- | --- | --- |
| linear phosphines, 1a–c | 38.9 | 29.8 | 13.9 |
| linear phosphine oxides, 11a–c | 37.7 | 28.3 | 10.6 |
| branched phosphines, 5a–c | 42.5 | 30.0 | 12.6 |
| branched phosphine oxides 12a–c | 38.9 | 27.9 | 9.1 |

[a]Gradient t = 0 min, 80% MeOH; 20% $H_2O$; t = 30 min, 100% MeOH; t = 60 min, 90% MeOH, 10% THF The phosphine oxides reliably eluted 1–3 min before the analogous phosphines. This is because the phosphine oxides have a lower fluorine content (on a percentage basis) than the phosphines, and (probably more importantly) because they are more polar. (Fluorous silica tends to effect polar/non-polar separation in a reverse phase fashion.) The comparison of the linear and branched compounds is more interesting. With one fluorous tag, the branched compound 5c emerges about 1 min before the linear 1c; with two tags, the retention times of 5b and 1b are nearly identical, and with 3 tags, the linear compound 1a emerges almost 4 min before the branched 5a. The trend for the corresponding phosphine oxides is similar.

Liquid-liquid partition coefficients for all six phosphines between FC-72 and three organic solvents (methanol, THF, and toluene) were also measured. The procedure involved a simple partitioning followed by HPLC analysis. Measurements were reproducible within 10% or less, and the data are shown in Table 2.

Only the triply fluorous phosphines 1a and 5a show sufficiently high partition coefficients for convenient separation by liquid-liquid extraction, and only against methanol (other polar organic solvents may also be suitable). THF has good dissolving power for fluorous compounds and not surprisingly provides low partition coefficients. Toluene is a very fluorophobic solvent with respect to fluorous tin reagents [(RfCH$_2$CH$_2$)$_3$SnX], but it has good dissolving power in these phosphines (presumably due to the aromatic rings), so low partition coefficients result. Van Koten and co-workers have recently reported examples where compounds with more fluorous chains had lower partition coefficients than those with fewer, and this phenomenon was also observed in the present studies.

TABLE 2

Partition Coefficients of Fluorous Aryl Phosphines at Room Temperature in 50/50 (v/v) of FC-72/Organic Solvents (P = c$_{fluorous\ phase}$/c$_{organic\ phase}$)

| compound | F content (wt %) | FC-72/methanol | FC-72/THF | FC-72/toluene |
|---|---|---|---|---|
| 1a | 57 | 30.03 | 0.08 | 0.75 |
| 1b | 52 | 1.86 | 0.05 | 0.05 |
| 1c | 41 | 0.12 | 0.02 | 0.05 |
| 5a | 59 | 18.48 | 0.51 | 6.84 |
| 5b | 53 | 3.34 | 1.05 | 0.18 |
| 5c | 42 | 0.09 | 0.01 | 0.12 |

Figure 7:
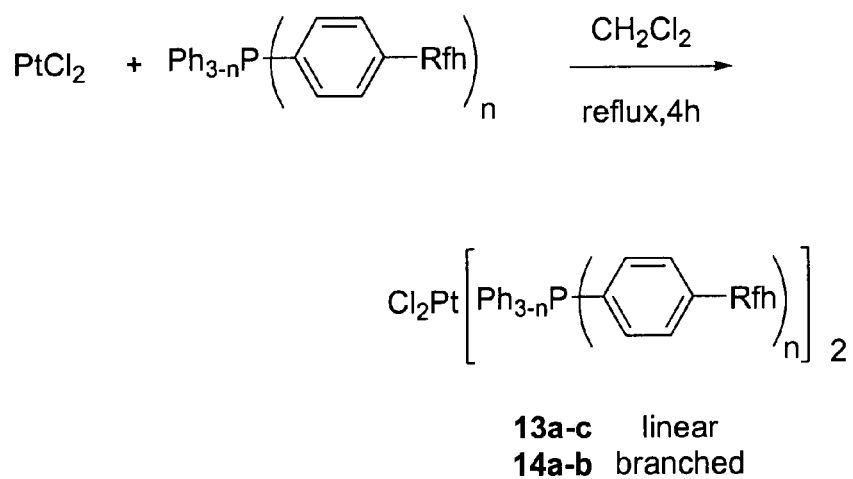
FIG. 7 illustrates preparation of platinum catalysts from fluorous phosphines by reaction of the fluorous phosphines with platinum dichloride.

Platinum catalysts were prepared from all six of the phosphines by reaction with platinum dichloride, as shown in FIG. 7. The catalysts were isolated in excellent yields (82–86%) as white or yellow solids after recrystallization from dichloromethane/ether, and each exhibited the expected molecular ion peak in the mass spectrum. The fluorous catalysts exhibited good organic solubility and promoted allylations of aldehydes with a fluorous allylstannane. The fluorous components of the reaction mixtures (including the catalyst remnants) were removed by solid phase extraction.

The present invention thus provides practical methods to synthesize novel branched fluorous triarylphosphines bearing one, two or three fluorous tags. The fluorous phosphines and metal complexes derived therefrom of the present invention are well retained on fluorous reverse phase silica gel under conditions where most organic compounds elute with the solvent front. The use of solid phase extractions allows reduction of the fluorous content of a tagged molecule, which is helpful in discovery-oriented synthesis and parallel synthesis as it allows one to simply adopt standard reaction conditions. There is no need to search for suitable fluorinated solvents or cosolvents. In the fluorous biphasic catalysis area, the trend is towards synthesizing phosphines with more fluorines, and the present invention provides new highly fluorous branched phosphines. In addition, "lightly fluorous" phosphines such as those provided in the present invention are separable by fluorous solid phase extraction.

EXAMPLES

General

All air and/or moisture-sensitive reactions were run under an atmosphere of argon. Tetrahydrofuran (THF) and diethyl ether were freshly distilled from sodium benzophenone ketyl under nitrogen. Methylene chloride and N,N-dimethylformamide (DMF) were distilled from calcium hydride under nitrogen. HPLC analysis was performed on a Millenium system using a Fluofix™ 12 0E column with detection by UV.

Example 1

1-Bromo-4-(3,3,4,4,5,5,6,6,7,7,8,8,8-tridecafluorooctyl) benzene (8)

To a 250 mL three-neck flask equipped with dropping funnel was added zinc powder (9.50 g, 146.2 mmol) and dry THF (20 mL) under argon. 1,2-Dibromoethane (0.5 mL) was added and the mixture was heated at 65° C. for 2 min. The mixture was then cooled to room temperature. Chlorotrimethylsilane (0.5 mL) was added and the mixture was stirred at room temperature for 20 min. A solution of 3,3,4,4,5,5,6,6,7,7,8,8,8-tridecafluorooctyl iodide (57.8 g, 126.6 mmol) in dry THF (100 mL) was added dropwise to keep the temperature of the solution at room temperature. The reaction mixture was stirred at room temperature for 12 h. The colorless solution was then transferred via canula to a solution of 1-bromo-4-iodobenzene (35.8 g, 126.6 mmol) and tetrakis(triphenylphosphine) palladium(0) (5.0 g, 4.3 mmol) in THF (60 mL). After 24 h at 45° C., the solvent was removed under vacuum. The residue was dissolved in methylene chloride (50 mL), extracted with FC-72 (50 mL) six times. The combined FC-72 layers were concentrated. Vacuum distillation of the residue gave 8 (34.3 g, 56%) as a colorless liquid. b.p. 79.1–80.9° C./0.03 mmHg; $^1$H NMR (300 MHz, CDCl$_3$) δ2.36 (tt, J=18.3, 9.1 Hz, 2H), 2.86–2.92 (m, 2H), 7.11 (d, J=8.4 Hz, 2H), 7.45 (d, J=8.4 Hz, 2H); $^{13}$C NMR (75 MHz, CDCl$_3$) δ26.1, 32.9 (t, J$_{FC}$=22.1 Hz), 105.5–123.2 (m, C$_6$F$_{13}$), 120.7, 130.1, 132.1, 138.3; $^{19}$F NMR (282.4 MHz, CDCl$_3$) δ–125.6 (2F), –122.9 (2F), –121.7 (2F), –120.7 (2F), –113.4 (2F), –79.6 (3F); IR (CHCl$_3$) 3065, 2954, 2879, 1490, 1237, 1145, 1013, 810 cm$^{-1}$; EIMS m/z 502/504 (M$^+$), 423, 169/171 (M—C$_6$F$_{13}$CH$_2$)$^+$.

Example 2

1-Bromo-4-(3,3,4,4,5,5,5-heptafluoro-2,2-bis-trifluoromethylpentyl)benzene (10)

A 250 mL three-neck flask was charged with perfluoro-2-methylpent-2-ene (27.0 g, 90 mmol), dry cesium fluoride (13.4 g, 88 mmol) and dry DMF (65 mL) under argon. The solution was stirred at 45° C. for 36 h. 4-Iodobenzyl bromide (17.8 g, 59.9 mmol) was added, and the mixture was heated at 65° C. for 14 h. The mixture was cooled to room temperature and poured into a 2 L separatory funnel with 1200 mL water. The organic layer was dried and evaporated and the residue was loaded onto a silica gel column. Eluting with hexane-ethyl acetate (40:1) gave 10 (26.1 g, 89%) as a pale yellow liquid. $^1$H NMR (300 MHz, CDCl$_3$) δ3.43 (s, 2H), 7.17 (d, J=8.4 Hz, 2H), 7.45 (d, J=8.4 Hz, 2H); $^{13}$C NMR (75 MHz, CDCl$_3$) δ32.2, 61.6(sept, J$_{FC}$=24.7 Hz), 109.6–123.5 (m, C$_3$F$_7$), 122.1 (q, J$_{FC}$=287.9 Hz), 122.7, 130.1, 131.6, 133.3; $^{19}$F NMR (282.4 MHz, CDCl$_3$) δ–125.0 (2F), –104.9 (2F), –79.3 (3F), –61.3 (6F); IR (CHCl$_3$) 3062, 2985, 1596, 1494, 1332, 1257, 1111, 980, 885, 836, 746, 702 cm$^{-1}$; EIMS m/z 488/490 (M$^+$), 169/171 (M—C$_6$F$_{13}$)$^+$.

Example 3

Tris-[4-(3,3,4,4,5,5,6,6,7,7,8,8,8-tridecafluorooctyl)phenyl] phosphane (1a)

A solution of t-BuLi (1.7M in pentane, 5.6 mL, 9.5 mmol) was added slowly to 1-bromo-4-(3,3,4,4,5,5,6,6,7,7,8,8,8-tridecafluorooctyl)benzene 8 (2.45 g, 4.9 mmol) in ether (150 mL) at –78° C. After stirring at –78° C. for 30 min, phosphorus trichloride (0.14 mL, 1.6 mmol) was added. The mixture was warmed to room temperature over 2 h and stirred at room temperature for 2 h. The reaction mixture was then quenched with water (5 mL). The ether layer was separated. The aqueous layer was further extracted with ether (10 mL) 3 times. The ether layers were combined, dried over magnesium sulfate and concentrated under vacuum. The residue was then purified by column chromatography (20:1, hexanes/ethyl acetate) on silica gel to yield 1a (1.58 g, 76%) as a pale yellow solid: m.p. 49.9–52.4° C.; $^1$H NMR (300 MHz, CDCl$_3$) δ2.38 (tt, J=18.0, 8.7 Hz, 6H), 2.90–2.96 (m, 6H), 7.19–7.29 (m, 12H); $^{13}$C NMR (75 MHz, CDCl$_3$) δ26.4, 32.9 (t, J$_{FC}$=21.8 Hz), 107.7–121.5 (m, C$_6$F$_{13}$), 128.7 (d, J$_{PC}$=7.0 Hz), 134.6 (d, J$_{PC}$=18.8 Hz), 135.7 (d, J$_{PC}$=10.5 Hz), 140.2; $^{19}$F NMR (282.4 MHz, CDCl$_3$) δ−126.7 (6F), −124.0 (6F), −123.4 (6F), −122.4 (6F), −115.2 (6F), −81.3 (9F); $^{31}$P NMR (121.5 MHz, CDCl$_3$) δ−6.65 (s); EIMS m/z 1300 (M$^+$), 877, 513.

Example 4

Phenyl-bis-[4-(3,3,4,4,5,5,6,6,7,7,8,8,8-tridecafluorooctyl) phenyl]phosphane (1b)

This was synthesized in a manner similar to 1a as a white solid: mp 42.1–43.1° C.; 90%, $^1$H NMR (300 MHz, CDCl$_3$) δ2.31–2.48 (m, 4H), 2.91–2.97 (m, 4H), 7.20–7.36 (m, 13H); $^{13}$C NMR (75 MHz, CDCl$_3$) δ26.3, 32.8 (t, J$_{FC}$=22.5 Hz), 105.2–121.4 (m, C$_6$F$_{13}$), 128.5, 128.6, 128.9, 133.6 (d, J$_{PC}$=19.5 Hz), 134.2 (d, J$_{PC}$=19.5 Hz), 135.5 (d, J$_{PC}$=9.5 Hz), 137.0 (d, J$_{PC}$=9.5 Hz), 139.9; $^{19}$F NMR (282.4 MHz, CDCl$_3$) δ−124.8 (4F), −122.3 (4F), −121.8 (4F), −120.7 (4F), −113.3 (4F), −79.7 (6F); $^{31}$P NMR (121.5 MHz, CDCl$_3$) δ−5.91 (s); EIMS m/z 954 (M$^+$), 531, 477; HRMS for C$_{34}$H$_{21}$F$_{26}$P, calcd: 954.0961; found: 954.0950.

Example 5

Diphenyl-[4-(3,3,4,4,5,5,6,6,7,7,8,8,8-tridecafluorooctyl) phenyl]phosphane (1c)

This was synthesized in a manner similar to 1a: Oil, 81%, $^1$H NMR (300 MHz, CDCl$_3$) δ2.31–2.50 (m, 2H), 2.92–3.05 (m, 2H), 7.23–7.26 (m, 2H), 7.33–7.41 (m, 12H); $^{13}$C NMR (75 MHz, CDCl$_3$) δ26.4, 32.9 (t, J$_{FC}$=21.7 Hz), 107.7–119.3 (m, C$_6$F$_{13}$), 128.6, 128.7, 128.9, 133.8 (d, J$_{PC}$=19.5 Hz), 134.4 (d, J$_{PC}$=19.5 Hz), 135.7 (d, J$_{PC}$=10.5 Hz), 139.9; $^{19}$F NMR (282.4 MHz, CDCl$_3$) δ−125.0 (2F), −122.3 (2F), −121.7 (2F), −120.7 (2F), −113.5 (2F), −79.7 (3F); $^{31}$P NMR (121.5 MHz, CDCl$_3$) δ−5.11 (s); EIMS m/z 608 (M$^+$), 183, 108.

Example 6

Tris-[4-(3,3,4,4,5,5,5-heptafluoro-2,2-bis-trifluoromethylpentyl)phenyl]phosphane (5a)

This was synthesized in a manner similar to 1a: Oil, 49%, $^1$H NMR (300 MHz, CDCl$_3$) δ3.54 (s, 6H), 7.33–7.44 (m, 12H); $^{13}$C NMR (75 MHz, CDCl$_3$) δ32.4, 61.7 (sept, J$_{FC}$=24.1 Hz), 109.6–123.8 (m, C$_3$F$_7$), 122.1 (q, J$_{FC}$=287.4 Hz), 131.7 (d, J$_{PC}$=5.0 Hz), 132.0, 133.4 (d, J$_{PC}$=19.5 Hz), 137.1 (d, J$_{PC}$=12.0 Hz); $^{19}$F NMR (282.4 MHz, CDCl$_3$) δ−121.9 (6F), −105.0 (6F), −79.2 (9F), −61.4 (18F); $^{31}$P NMR (121.5 MHz, CDCl$_3$) δ−7.12 (s); EIMS m/z 1258 (M$^+$), 939, 849.

Example 7

Phenyl-bis-[4-(3,3,4,4,5,5,5-heptafluoro-2,2-bis-rifluoromethylpentyl)phenyl]phosphane (5b)

This was synthesized in a manner similar to 1a: Oil, 68%, $^1$H NMR (300 MHz, CDCl$_3$) δ3.55 (s, 4H), 7.20–7.39 (m, 13H); $^{13}$C NMR (75 MHz, CDCl$_3$) δ32.5, 61.6 (sept, J$_{FC}$=24.1 Hz), 109.4–123.1 (m, C$_3$F$_7$), 122.0 (q, J$_{FC}$=288.0 Hz), 128.6 (d, J$_{PC}$=6.7 Hz), 129.1, 131.6, 132.0 (d, J$_{PC}$=10.5 Hz), 133.4 (d, J$_{PC}$=19.5 Hz), 133.9 (d, J$_{PC}$=20.0 Hz), 136.4 (d, J$_{PC}$=10.5 Hz), 137.3 (d, J$_{PC}$=11.9Hz); $^{19}$F NMR (282.4 MHz, CDCl$_3$) δ−121.7 (4F), −104.9 (4F), −78.8 (6F), −61.1 (12F); $^{31}$P NMR (121.5 MHz, CDCl$_3$) δ−6.29 (s); EIMS m/z 926 (M$^+$), 608, 517, 197.

Example 8

Diphenyl-[4-(3,3,4,4,5,5,5-heptafluoro-2,2-bis-trifluoromethylpentyl)phenyl]phosphane (5c)

This was synthesized in a manner similar to 1a: Oil, 51%, $^1$H NMR (300 MHz, CDCl$_3$) δ3.59 (s, 2H), 7.26–7.41 (m, 14H); $^{13}$C NMR (75 MHz, CDCl$_3$) δ32.5, 61.6 (sept, J$_{FC}$=24.1 Hz), 105.6–119.8 (m, C$_3$F$_7$), 122.0 (q, J$_{FC}$=288.1 Hz), 128.6 (d, J$_{PC}$=7.0 Hz), 129.0, 131.5 (d, J$_{PC}$=22.3 Hz), 132.1 (d, J$_{PC}$=9.5 Hz), 133.4 (d, J$_{PC}$=19.0 Hz), 133.8 (d, J$_{PC}$=19.5 Hz), 136.8 (d, J$_{PC}$=10.5 Hz), 137.6 (d, J$_{PC}$=11.7 Hz); $^{19}$F NMR (282.4 MHz, CDCl$_3$) δ−121.8 (2F), −104.9 (2F), −79.1 (3F), −61.2 (6F); $^{31}$P NMR (121.5 MHz, CDCl$_3$) δ−5.39 (s); EIMS m/z 594 (M$^+$), 275, 183.

Example 9

Bis-{tris-[4-(3,3,4,4,5,5,6,6,7,7,8,8,8-tridecafluorooctyl) phenyl]phosphine}platinum dichloride (13a)

Platinum dichloride (50 mg, 0.19 mmol) was heated with 1a (520 mg, 0.40 mmol) under reflux in methylene chloride (4 mL) for 4 h. The mixture was cooled to room temperature and methylene chloride (10 mL) was added. After filtration and concentration, the solid was recrystallized in methylene chloride-ether to give 13a (460 mg, 85.4%): m.p. 179.1–180.9° C.; $^1$H NMR (300 MHz, CDCl$_3$) δ2.35 (tt, J=18.3, 8.7 Hz, 12H), 2.88–2.93 (m, 12H), 7.03 (d, J=6.9 Hz, 12H), 7.41 (dd, J=11.1, 8.2 Hz, 12H); $^{13}$C NMR (125 MHz, CDCl$_3$) δ26.3, 32.2 (t, J$_{FC}$=22.5 Hz), 108.3–120.0 (m, C$_6$F$_{13}$), 127.7 (d, J$_{PC}$=67.5 Hz), 127.8, 135.2, 142.3; $^{19}$F NMR (282.4 MHz, CDCl$_3$) δ−125.1 (12F), −122.4 (12F), −121.8 (12F), −120.8 (12F), −113.3 (12F), −79.6 (18F); $^{31}$P NMR (121.5 MHz, CDCl$_3$) δ13.7 (s, J$_{PtP}$=3679 Hz); IR (neat) 2953, 2917, 2848, 1456, 1204, 1143, 811, 744, 700 cm$^{-1}$; EIMS m/z 2866 (M$^+$), 2832 (M—Cl)$^+$, 2796 (M—2Cl)$^+$.

Example 10

Bis-{Phenyl-bis-[4-(3,3,4,4,5,5,6,6,7,7,8,8,8-tridecafluorooctyl)phenyl]phosphine}platinum dichloride (13b)

This was synthesized in a manner similar to 13a: 83%, m.p. 196.8–198.2° C.; $^1$H NMR (300 MHz, CDCl$_3$) δ2.35 (tt, J=17.6, 9.0 Hz, 8H), 2.88–2.93 (m, 8H), 7.03–7.47 (m, 26H); $^{13}$C NMR (75 MHz, CDCl$_3$) δ26.2, 32.2 (t, J$_{FC}$=21.9 Hz), 110.6–121.3 (m, C$_6$F$_{13}$), 127.8 (d, J$_{PC}$=67.3 Hz), 127.4–128.3 (m), 129.2 (d, J$_{PC}$=65.6 Hz), 134.6, 135.3, 142.3; $^{19}$F NMR (282.4 MHz, CDCl$_3$) δ−125.0 (8F), −122.4 (8F), −121.8 (8F), −120.8 (8F), −113.3 (8F), −79.6 (12F); $^{31}$P NMR (121.5 MHz, CDCl$_3$) δ14.2 (s, J$_{PtP}$=3671 Hz); IR (neat) 3058, 2928, 2858, 1601, 1482, 1436, 1198, 744, 696 cm$^{-1}$; EIMS m/z 2174 (M$^+$), 2103 (M-2Cl)$^+$.

Example 11

Bis-{Diphenyl-[4-(3,3,4,4,5,5,6,6,7,7,8,8,8-tridecafluorooctyl)phenyl]phosphine}platinum dichloride (13c)

This was synthesized in a manner similar to 13a: 85%, m.p. 230.2–231.6° C.; $^1$H NMR (300 MHz, CDCl$_3$) δ2.35 (tt, J=18.0, 9.1 Hz, 4H), 2.88–2.93 (m, 4H), 7.04–7.51 (m, 28H); $^{13}$C NMR (75 MHz, CDCl$_3$) δ26.2, 32.3 (t, J$_{FC}$=21.9 Hz), 104.8–123.2 (m, C$_6$F$_{13}$), 127.6–129.8 (m), 130.9, 134.7, 135.4, 142.1; $^{19}$F NMR (282.4 MHz, CDCl$_3$) δ−125.0 (4F), −122.3 (4F), −121.7 (4F), −120.7 (4F), −113.3 (8F), −79.7 (6F); $^{31}$P NMR (121.5 MHz, CDCl$_3$) δ14.7 (s, J$_{PtP}$=3673 Hz); IR (neat) 3060, 2959, 1601, 1482, 1436, 1237, 1197, 744, 696 cm$^{-1}$; FABMS m/z 1447 (M—Cl)$^+$, 1410 (M-2Cl)$^+$.

Example 12

Bis-{tris-[4-(3,3,4,4,5,5,5-heptafluoro-2,2-bis-trifluoromethylpentyl)phenyl]phosphine}platinum dichloride (14a)

This was synthesized in a manner similar to 13a: 82%, m.p. 238.6–241.2° C.; $^1$H NMR (300 MHz, CDCl$_3$) δ3.50 (s, 12H), 7.13–7.15 (m, 12H), 7.34–7.37 (m, 12H); $^{13}$C NMR (75 MHz, CDCl$_3$) δ32.2, 60.6–62.0 (m), 104.8–123.2 (m, C$_3$F$_7$), 121.9 (q, J$_{FC}$=289.2 Hz), 128.8, 129.7, 131.1, 134.7; $^{19}$F NMR (282.4 MHz, CDCl$_3$) δ−121.8 (12F), −105.0 (12F), −78.6 (18F), −60.1 (36F); $^{31}$P NMR (121.5 MHz, CDCl$_3$) δ13.7 (s, J$_{PtP}$=3638 Hz); EIMS m/z 2783 (M$^+$) 2712 (M-2Cl)$^+$; HRMS for C$_{78}$H$_{36}$F$_{78}$P$_2$Cl$_2$Pt, calcd: 2780.005; found: 2780.0156; IR (neat) 2951, 2923, 2866, 1454, 1411, 1333, 1242, 741, 678 cm$^{-1}$.

Example 13

Bis-{phenyl-bis-[4-(3,3,4,4,5,5,5-heptafluoro-2,2-bis-trifluoromethylpentyl)phenyl]phosphine}platinum dichloride (14b)

This was synthesized in a manner similar to 13a: 86%, m.p. 227.4–228.9° C.; $^1$H NMR (300 MHz, CDCl$_3$) δ3.51 (s, 8H), 7.10–7.50 (m, 26H); $^{13}$C NMR (75 MHz, CDCl$_3$) δ32.3, 61.5 (sept, J$_{FC}$=24.8 Hz), 104.8–123.2 (m, C$_3$F$_7$), 121.9 (q, J$_{FC}$=288.4 Hz), 128.0, 128.1, 129.0, 129.9, 131.2, 134.2, 134.4, 134.9; $^{19}$F NMR (282.4 MHz, CDCl$_3$) δ−121.9 (8F), −105.0 (8F), −79.0 (12F), −61.2 (24F); $^{31}$P NMR (121.5 MHz, CDCl$_3$) δ14.3 (s, J$_{PtP}$=3652 Hz); EIMS m/z 2118 (M$^+$) 2086 (M—Cl)$^+$; HRMS for C$_{64}$H$_{34}$F$_{52}$P$_2$Cl$_2$Pt, calcd: 2116.0309; found: 2116.0212; IR (neat) 3060, 2982, 1602, 1565, 1500, 1333, 1245, 1109, 741, 677 cm$^{-1}$.

Although the present invention has been described in detail in connection with this summary and the examples referenced above, it is to be understood that such detail is solely for that purpose and that variations can be made by those skilled in the art without departing from the spirit of the invention.

What is claimed is:

1. A chemical compound having the formula:

$$R_{3-n}-\overset{O}{\underset{\|}{P}}-\left(\phantom{x}\!\!\!\!\!\bigcirc\!\!\!\!\!\phantom{x}\text{—RsRf}\right)_n$$

wherein R is an alkyl group or an aryl group, n is 1, 2 or 3, Rs is a spacer group and Rf is a branched fluorous group.

2. The chemical compound of claim 1 wherein Rs is (—CH$_2$—)$_x$ and x is an integer in the range of 1 to 12.

3. The chemical compound of claim 1 wherein Rs is (—CH$_2$—)$_x$ and x is an integer in the range of 1 to 6.

4. The chemical compound of claim 3 wherein x is 1.

5. The chemical compound of claim 2 wherein Rf is a branched hydrofluoroalkyl group or a branched perfluoroalkyl group.

6. The chemical compound of claim 5 wherein Rf is branched at a carbon atom adjacent Rs such that there is no fluorine atom β to the carbon atom of Rs attached to Rf.

7. The chemical compound of claim 6 wherein Rf is —CRf$^1$Rf$^2$(CF$_2$Rf$^3$) wherein Rf$^1$, Rf$^2$ and Rf$^3$ are independently a hydrofluoroalkyl group, a perfluoroalkyl group, Rf$^1$ and Rf$^2$ form a hydrofluoroalkyl ring or a perfluoroalkyl ring of 3 to 12 members, or Rf$^1$ and Rf$^3$ form a hydrofluoroalkyl ring or a perfluoroalkyl ring of 3 to 12 members.

8. The chemical compound of claim 5 wherein Rf is branched such that there is no fluorine atom β to a C—H bond.

9. The chemical compound of claim 5 wherein R is a phenyl group.

10. A chemical compound having the formula:

$$R_{3-n}-P-\left(\phantom{x}\!\!\!\!\!\bigcirc\!\!\!\!\!\phantom{x}\text{—RsRf}\right)_n$$

wherein R is an alkyl group or a aryl group, n is 1, 2 or 3, Rs is a spacer group and Rf is a branched fluorous group.

11. The chemical compound of claim 10 wherein Rs is (—CH$_2$—)$_x$ and x is an integer in the range of 1 to 12.

12. The chemical compound of claim 10 wherein Rs is (—CH$_2$—)$_x$ and x is an integer in the range of 1 to 6.

13. The chemical compound of claim 12 wherein x is 1.

14. The chemical compound of claim 11 wherein Rf is a branched hydrofluoroalkyl group or a branched perfluoroalkyl group.

15. The chemical compound of claim 14 wherein Rf is branched at a carbon atom adjacent Rs such that there is no fluorine atom β to the carbon atom of Rs attached to Rf.

16. The chemical compound of claim 15 wherein Rf is —CRf$^1$Rf$^2$(CF$_2$Rf$^3$) wherein Rf$^1$, Rf$^2$ and Rf$^3$ are independently a hydrofluoroalkyl group, a perfluoroalkyl group, Rf$^1$ and Rf$^2$ form a hydrofluoroalkyl ring or a perfluoroalkyl ring of 3 to 12 members, or Rf$^1$ and Rf$^3$ form a hydrofluoroalkyl ring or a perfluoroalkyl ring of 3 to 12 members.

17. The chemical compound of claim 14 wherein Rf is branched such that there is no fluorine atom β to a C—H bond.

18. The chemical compound of claim 14 wherein R is a phenyl group.

19. A method of increasing the fluorous nature of a compound, including the step of reacting the compound with a second compound having the formula:

$$R_{3-n}-P-\left(\phantom{x}\!\!\!\!\!\bigcirc\!\!\!\!\!\phantom{x}\text{—RsRf}\right)_n$$

wherein R is an alkyl group or an aryl group, n is 1, 2 or 3, Rs is a spacer group and Rf is a branched fluorous group.

20. A method of increasing the fluorous nature of a compound, including the step of reacting the compound with a second compound having the formula:

$$R_{3-n}-\overset{O}{\underset{\|}{P}}-\left(\phantom{x}\!\!\!\!\!\bigcirc\!\!\!\!\!\phantom{x}\text{—RsRf}\right)_n$$

wherein R is an alkyl group or an aryl group, n is 1, 2 or 3, Rs is a spacer group and Rf is a branched fluorous group.

21. A metal complex comprising a metal and at least one phosphine oxide of claim 1.

22. The metal complex of claim 21 wherein the metal is rhodium, platinum, paladium, nickel, iron, ruthenium, osmium, cobalt or iridium.

23. A metal complex comprising a metal and at least one phosphine of claim 10.

24. The metal complex of claim 22 wherein the metal is rhodium, platinum, paladium, nickel, iron, ruthenium, osmium, cobalt or iridium.

25. A method of synthesizing a branched fluorous phosphine comprising the steps of: reacting a fluoroalkene with a metal fluoride; adding an alkylating agent to produce a fluorous halo arene; converting the fluorous halo arene to an organometallic derivative thereof; and reacting the organometallic derivative with $R_{3-n}P(Z^3)_n$ wherein $Z^3$ is a leaving group an wherein R is an alkyl group or an aryl group.

26. The method of claim 25 wherein the fluoroalkene has the formula:

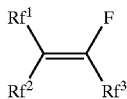

wherein $Rf^1$, $Rf^2$ and $Rf^3$ are independently a hydrofluoroalkyl group, a perfluoroalkyl group, $Rf^1$ and $Rf^2$ form a hydrofluoroalkyl ring or a perfluoroalkyl ring of 3 to 12 members, or $Rf^1$ and $Rf^3$ form a hydrofluoroalkyl ring or a perfluoroalkyl ring of 3 to 12 members.

27. The method of claim 26 wherein the alkylating agent has the formula:

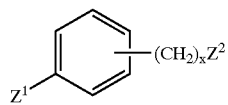

wherein $Z^1$ is bromine or iodine and $Z^2$ is a leaving group.

28. The method of claim 27 wherein the fluorous halo arene has the formula:

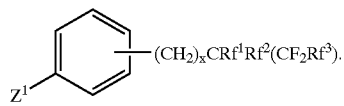

29. The method of claim 25 wherein the fluorous halo arene is converted to an organometallic derivative thereof via metallation or halogen-metal exchange.

* * * * *